United States Patent [19]

Okada et al.

[11] Patent Number: 4,790,331

[45] Date of Patent: Dec. 13, 1988

[54] METHOD FOR PLACEMENT OF CATHETER IN A BLOOD VESSEL

[75] Inventors: Yosuke Okada; Munehito Kurimoto, both of Shizuoka,, Japan

[73] Assignee: Sherwood Medical Company, St. Louis, Mo.

[21] Appl. No.: 936,854

[22] Filed: Dec. 2, 1986

[51] Int. Cl.⁴ .............................................. A61M 25/00
[52] U.S. Cl. ...................................... 128/772; 604/53; 604/95
[58] Field of Search ................................ 128/656–658, 128/772; 604/95, 170, 281, 51–53

[56] References Cited

U.S. PATENT DOCUMENTS

| 2,118,631 | 5/1938 | Wappler | 604/170 |
| 2,857,915 | 10/1958 | Sheridan | 604/658 |
| 3,416,531 | 12/1968 | Edwards | 604/95 |
| 3,547,103 | 12/1970 | Cook | 604/95 |
| 4,020,829 | 5/1977 | Willson et al. | 604/95 X |
| 4,619,644 | 10/1986 | Scott | 604/53 |
| 4,723,550 | 2/1988 | Bales et al. | 604/256 X |
| 4,724,846 | 2/1988 | Evans | 128/772 |
| 4,726,374 | 2/1988 | Bales et al. | 604/348.1 |

Primary Examiner—Dalton L. Truluck
Attorney, Agent, or Firm—Stanley N. Garber; Andrew J. Beck; Montgomery W. Smith

[57] ABSTRACT

The present invention provides a catheter assembly for placement in a blood vessel which comprises a catheter body having an opening at the distal tip thereof and provided with a luer-connector at proximal portion and a flexible guide wire inserted into said catheter body and bendingly formed to be J-shaped at the distal tip thereof.

3 Claims, 2 Drawing Sheets

METHOD FOR PLACEMENT OF CATHETER IN A BLOOD VESSEL

BACKGROUND OF THE INVENTION (1) Field of the Invention

This invention relates to a catheter assembly and method for guiding a tip of a catheter within a blood vessel to an objective position.

(2) Description of the Prior Art

Recently, central venous catheters have been widely used for the purposes of hyperalimentation, measurement of central venous pressure, administration of chemotherapeutic, pressor, and vasopressor drugs, and emergency securing of an intravenous delivery route. Further, when inserting a catheter into a central blood vessel, the percutaneous catheterization method using a cannula made of plastic has been generally employed in place of the more conventional cut down method.

In the venipuncture for the percutaneous catherization method, the injective routes are cephalic vein, median cubital vein, internal jugular vein, subclavian vein, or external jugular vein.

When using the internal jugular vein as the insertion route, it is difficult to insert the catheter, and higher incidence of serious complications, such as carotid arterial injection, fistula of thoracic duct, hemothorax, or pneumothorax may result.

Although the catheter can be easily inserted when using the subclavian vein as an insertion route, a smooth pass of the catheter at a branch portion of the blood vessel is difficult, which may result in the catheter being inadvertently positioned in the jugular vein, and in serious complications, such as pneumothorax, hemothorax, hydrothorax, hydromediastinosis or myocardial puncture. Insertion routes, such as via the cephalic vein or the median cubital vein, may result in less serious complications. However, because these routes require a special long catheter, and result in a high incidence of infection or complication of phlebitis, they are not favored.

Accordingly, in general, the external jugular vein is favorably adopted as an insertion route because it is easy to insert the catheter and operate it during insertion, the external jugular vein is the only site by which the central vein may be reached under visual observation, and complications rarely occur because this site is comparatively distant from other major organs.

Conventionally, when the above mentioned external jugular vein as is used as the insertion route, a catheter-assembly is used in the form of a guide wire inserted into the catheter, where the guide wire has less flexibility than the catheter. Thus, the catheter-assembly is inserted over a needle previously inserted into the blood vessel, and the catheter is guided into the intended position with the guide wire. After insertion, guide wire is withdrawn.

However, because the distal end portion of the guide wire in the conventional catheter assembly is straight, it is difficult to make the distal end portion of the catheter enter in the subclavian vein at the corresponding branched portion of the blood vessel, where the external jugular vein joins with the subclavian vein at an acute angle and the catheter must zigzag through a vein valve.

Further, insertion of the distal end portion of the catheter into the central vein is both difficult for the operator, and painful to the patient.

SUMMARY OF THE INVENTION

A catheter assembly according to this invention includes a catheter having an opening at a distal end thereof, a luer-connector at a proximal end thereof, a radiopaque line extending the full length of the catheter, and a flexible guide wire with a distal end portion thereof formed into a J-shape inserted in and through the catheter. The guide wire is less flexible than the catheter, such that when the J-shaped distal end portion of the guide wire is extended out of the distal end of the catheter, the catheter distal end portion is substantially straight, and when the J-shaped guide wire distal end portion is retracted within the catheter, the catheter distal end is curved.

BRIEF DESCRIPTION OF THE DRAWINGS

FIG. 4A shows the guide wire in the extended position for advancement along the vein, FIG. 4B shows the guide wire in the withdrawn position to curve the catheter distal end portion for guiding into a branch of the vein. FIG. 4C shows the catheter assembly advanced into the branch vein.

DETAILED DESCRIPTION OF THE INVENTION

Figure 1:
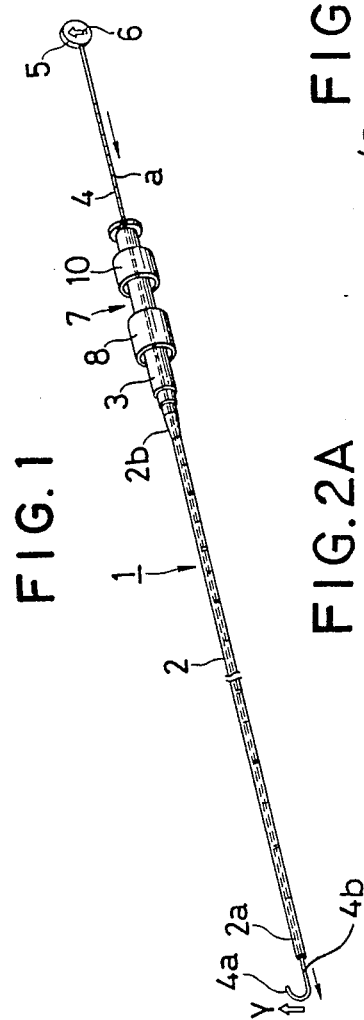
FIG. 1 is a perspective view of an embodiment of a catheter assembly according to this invention.
Figure 4A:
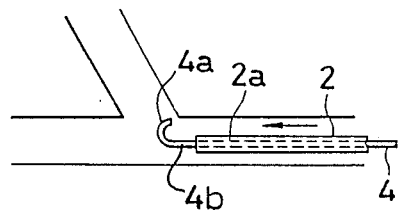
FIGS. 4A, 4B and 4C are schematic diagrams of a catheter and guide wire positioned within a vein.
Figure 4B:
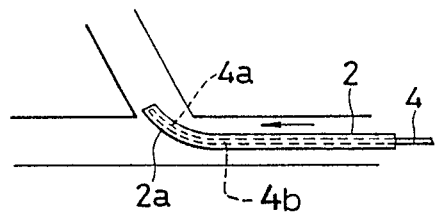
Figure 4C:
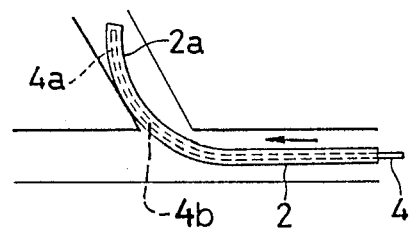

FIG. 1 shows a catheter assembly 1 according to this invention, including a flexible, normally straight catheter body 2, having radiopaque line in full length for radioscopy, and being provided with an opening at a tip or open distal end of a soft, flexible distal end length, or segment, or portion 2a of the catheter body and a luer-connector 3 at proximal end 2b of the catheter body. The catheter assembly further includes a flexible guide wire 4 inserted into the catheter body 2. A distal end portion 4a of the guide wire 4 is in a J-shape, and an intermediate portion 4b proximally contiguous to or adjoining or adjacent the distal end portion 4a is substantially straight when compared to the J-shaped portion, i.e., having a comparably smaller curvature, or a much greater radius, than the J-shaped distal end portion 4a. As shown in FIGS. 4A, 4B and 4C, the normal radius of curvature of the J-shaped distal end portion 4a is preferably less than half the diameter of the blood vessel being catheterized, such that when the intermediate portion 4b of the guide wire is straight, and the J-shaped distal portion 4a is in the extended position, the greatest width of the J-shaped distal portion is less than the diameter of the blood vessel to be catheterized. The J-shaped distal end portion 4a may be extended from within the catheter distal end portion 2a to protrude past the catheter tip, with the intermediate portion 4b postioned at the distal end portions 2a, or withdrawn or retracted into the distal end portion 2a of said catheter, by moving a plate handle 5 at the end of the guide wire extending from the catheter proximal end 2b either toward the catheter proximal end 2b, or away from the catheter proximal end 2b, respectively. On the handle 5, an indicating portion 6, shown by an arrow, indicates the direction in which the J-shaped distal end 4a of the guide wire 4 extends from the straight, intermediate portion 4b of the guide wire 4. In other words, for this embodiment, the arrow of the handle 5 and the guide wire, including the J-shaped portion 4a, are substantially coplanar. The J-shaped distal end portion 4a of the guide wire 4 is oriented in the same direction with respect to the central axis of the guide wire as the arrow on the handle 5.

Figure 2A:
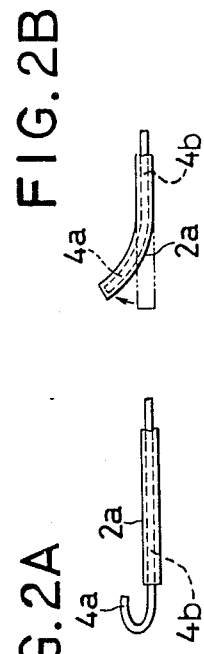
FIGS. 2A and 2B are detailed views of the distal end portion of the catheter assembly shown in FIG. 1, with the guide wire extended and retracted, respectively.
Figure 2B:
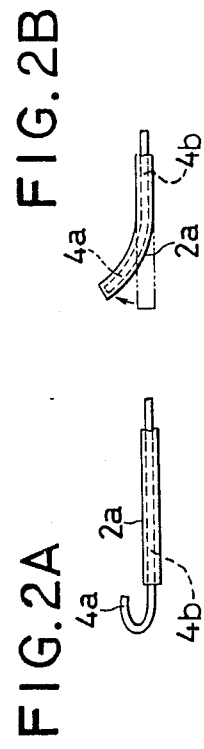

As shown in FIGS. 2A and 2B, the guide wire 4 maintains the distal end portion 2a of the catheter body 2 in a substantially straight condition when the J-shaped distal end portion 4a is extended from the distal end 2a of the catheter body 2 and the intermediate portion 4b of the guide wire 4 is positioned within the distal portion 2a of the catheter body 2 (see FIG. 2A), whereas the guide wire 4 maintains the distal end portion 2a of the catheter body 2 in a curved orientation with respect to the normally straight condition of the catheter body 2 when the tip of the J-shaped distal end portion 4a is retracted back into the distal end portion 2a of the catheter body 2 (see FIG. 2B).

Figure 3:
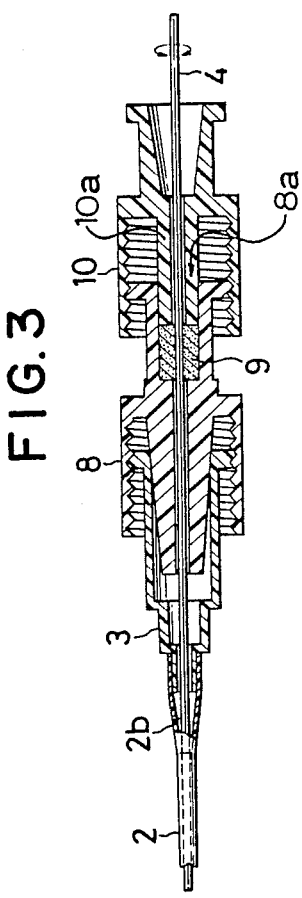
FIG. 3 is an axial section view of the locking mechanism of the catheter assembly shown in FIG. 1.

The locking mechanism of the catheter assembly 1 is shown in detail in FIG. 3, connected to the luer-connector 3 of the catheter body 2. Connector 8 of the locking mechanism is threadably engaged with the luer-connector 3. Functional body 10 is threadably engaged on an end of the connector 8 opposite the connection thereof to the luer connector 3, and includes projection 10a extending into recess 8a in the connector 8. Elastomer sleeve or body 9 is positioned within the recess 8a. The guide wire 4 is slidably inserted through a bore extending through the connector 8, elastomer sleeve 9, and functional body 10 in alignment with the bore of the catheter 2. As the body 10 is threaded onto the connector 8, the elastomer sleeve 9 is compressed within the recess 8a by the projection 10a to grip and frictionally fix the guide wire 4 within the locking mechanism. In FIG. 1, the letter "a" denotes graduations marked on the guide wire, e.g. at 50 mm intervals. These graduations facilitate quick and accurate confirmation of insertion depth of the guide wire 4.

As shown in FIG. 4A, when the catheter assembly 1 is inserted into a blood vessel, such as a vein, it enters and advances along the vein in a condition wherein the J-shaped distal end portion 4a of the guide wire 4 is in the extended position, with the intermediate portion 4b positioned in the distal end portion 2a of the catheter body 2 and the guide wire 4 fixed by the locking mechanism. When the J-shaped distal end portion 4a of the guide wire 4 is opposite, or the tip of the catheter distal end portion 2a nears, a branched portion of the blood vessel or a juncture of two blood vessels, the locking mechanism is loosened to free the guide wire 4, and the J-shaped distal end portion 4a of the guide wire 4 is withdrawn into the distal end portion 2a of the catheter body 2 to produce the curved condition shown in FIG. 4B. Then, the locking mechanism is again tightened to fix the guide wire 4 (see FIG. 4B). The operator may then control the bending direction with respect to the catheter body 2, or the curved orientation of the curved catheter distal end portion 2a, by rotating the handle 5, thereby being able to enter the branched portion of the blood vessel in an objective direction (see FIG. 4C).

The catheter can now be pushingly entered in the objective branched blood vessel easily and selectively (see FIG. 4C). The correct position of the catheter body 2 can be confirmed by radioscopy. Thus, the insertion of the catheter can be performed smoothly without causing pain to a patient, providing an excellent, practical effect.

What is claimed is:

1. A method for blood vessel catheterization using a catheter with a guide wire slidably inserted through a lumen through the catheter, comprising the steps of:

extending a J-shaped distal portion of the guide wire out of an open distal end of the catheter by sliding the guide wire within the catheter lumen to an extended position wherein the J-shaped distal portion of the guide wire is outside, and past the distal end of, the catheter and a comparably straight intermediate portion of the guide wire proximally adjoining the J-shaped distal portion is positioned within distal end portion of the catheter, and advancing the catheter and guide wire, with the guide wire in the extended position, within and along a first blood vessel until the distal end of the catheter is opposite a juncture of the first blood vessel with a second blood vessel; then retracting substantially all of the J-shaped distal portion of the guide wire within the catheter by sliding the guide wire within the catheter lumen to a retracted position wherein the J-shaped distal portion of the guide wire is within the distal end portion of the catheter.

rotating the guide wire, with the guide wire in the retracted position, until the distal end of the catheter is oriented toward the juncture of the second blood vessel, and advancing the distal end of the catheter, with the guide wire in the retracted position, into the second blood vessel.

2. The method of claim 1 with the additional steps of:

repeating the above steps in the indicated order until an objective position of the catheter distal end is reached; and then withdrawing the guide wire from the catheter.

3. The methodof claim 1 with the additional steps of, prior to each advancing step:

fixing the guide wire in slidable relation to the catheter.

* * * * *